United States Patent [19]
Luther et al.

[11] Patent Number: 6,090,370
[45] Date of Patent: Jul. 18, 2000

[54] USE OF SELECTED BENZOTRIAZOLE AND TRIAZINE DERIVATIVES FOR PROTECTING HUMAN HAIR FROM THE HARMFUL EFFECTS OF UV RADIATION

[75] Inventors: Helmut Luther, Grenzach-Wyhlen, Germany; René Baudin, Basel, Switzerland; Albert Stehlin, Rosenau, France; Jürg Haase, Bettingen, Switzerland

[73] Assignee: Ciba Specialty Chemicals Corporation, Tarrytown, N.Y.

[21] Appl. No.: 08/918,882

[22] Filed: Aug. 26, 1997

[30] Foreign Application Priority Data

Jun. 27, 1997 [CH] Switzerland .............................. 1561/97

[51] Int. Cl.⁷ ................................ A61K 7/42; A61K 7/00; A61K 31/53
[52] U.S. Cl. ............................... 424/59; 424/60; 424/400; 424/401; 514/242
[58] Field of Search ................................ 424/59, 60, 400, 424/401; 514/242

[56] References Cited

U.S. PATENT DOCUMENTS

| 4,680,144 | 7/1987 | Conner ........................................ 424/59 |
| 5,688,995 | 11/1997 | Luther et al. ............................... 562/30 |
| 5,843,193 | 12/1998 | Hawkins et al. ............................. 8/408 |

FOREIGN PATENT DOCUMENTS

| 0419164 | 3/1991 | European Pat. Off. . |
| 9304665 | 3/1993 | WIPO . |

OTHER PUBLICATIONS

"Photodegradation of hair and its photoprotection by a substantive photo filter" in Drug Cosm. Ind. (1995) 157(6), 28, 30, 32, 35–36, 38, 40, 42, 44.

*Primary Examiner*—Shelley A. Dodson
*Attorney, Agent, or Firm*—Kevin T. Mansfield

[57] ABSTRACT

Benzotriazole derivatives of formula

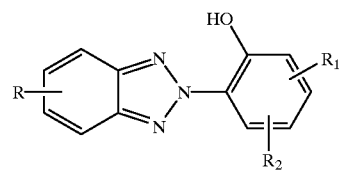

(1)

or triazines of formula

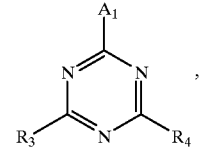

(2)

wherein R is hydrogen or chloro; $R_1$ is $C_1$–$C_{12}$alkyl or phenyl-$C_1$–$C_3$alkyl; $R_2$ is $C_1$–$C_4$alkyl or $SO_3M$; $A_1$ is a radical of formula

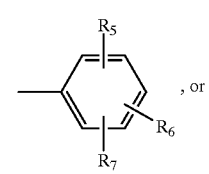

(2a)

, or (2b)

$R_3$ is a radical of formula

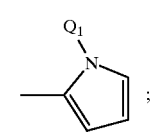

(2c)

$R_4$ is halogen; or a radical of formula

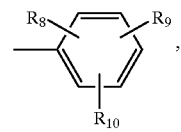

(2d)

$Q_1$ is $C_1$–$C_{18}$alkyl; $R_5$, $R_6$ and $R_7$ are each independently of one another hydrogen; $C_1$–$C_{12}$alkyl; $C_1$–$C_{18}$alkoxy; halogen; hydroxy; or a radical of formula

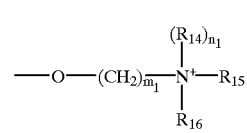

(2e)

Hal⁻; where the substituents are as defined herein, are distinguished by good substantivity for human hair while at the same time providing effective protection against UV radiation.

11 Claims, No Drawings

USE OF SELECTED BENZOTRIAZOLE AND TRIAZINE DERIVATIVES FOR PROTECTING HUMAN HAIR FROM THE HARMFUL EFFECTS OF UV RADIATION

The present invention relates to the use of selected benzotriazole and triazine derivatives for protecting human hair from the harmful effects of UV radiation.

If human hair is exposed to sunlight over a prolonged period of time it may be damaged in different ways. Under the influence of sunlight, dyed hair can change its colour and shade. Blond hair turns yellowish. The hair surface becomes rougher and at the same time drier. Furthermore, the hair gradually loses its sheen.

The use of UV absorbers can effectively protect natural and dyed hair from harmful sun radiation. Unfortunately, the UV absorbers employed so far have an insufficient fibre affinity on human hair, i.e. they can easily be washed out and therefore have only a short-term effect.

Surprisingly, it has now been found that specific benzotriazole and triazine derivatives have excellent substantivity for human hair while at the same time providing effective UV protection for hair.

Accordingly, this invention relates to the use of selected benzotriazole and triazine derivatives for protecting human hair from the harmful effects of UV radiation.

The selected benzotriazole compounds are 3-[2'H-benzotriazol-(2')-yl]-4-hydroxybenzene-sulfonic acids which conform to formula

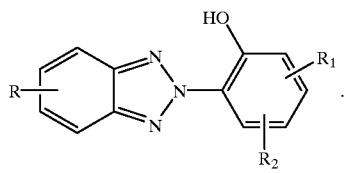

(1)

The selected triazine derivatives are compounds of formula

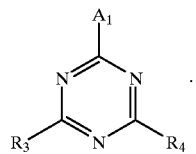

(2)

In formulae (1) and (2)

R is hydrogen or chloro, $R_1$ is $C_1$–$C_{12}$alkyl or phenyl-$C_1$–$C_3$alkyl;

$R_2$ is $C_1$ to $C_4$alkyl; or $SO_3M$;

$A_1$ is a radical of formula

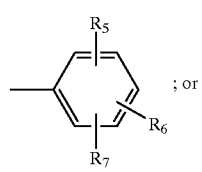

(2a)

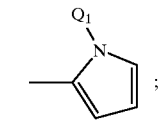

(2b)

$R_3$ is a radical of formula

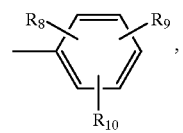

(2c)

$R_4$ is halogen; or a radical of formula

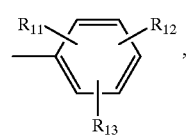

(2d)

$Q_1$ is $C_1$–$C_{18}$alkyl;

$R_5$, $R_6$ and $R_7$ are each independently of one another hydrogen; $C_1$–$C_{12}$alkyl; $C_1$–$C_{18}$alkoxy; halogen; hydroxy; or a radical of formula

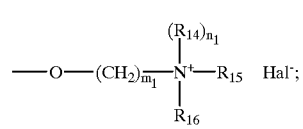

(2e)

$R_8$, $R_9$, $R_{10}$, $R_{11}$, $R_{12}$ and $R_{13}$ are each independently of one another hydrogen; hydroxy; $C_1$–$C_8$alkyl; $C_1$–$C_8$alkoxy; phenyl-$C_1$–$C_3$alkyl; $C_5$–$C_7$cyclohexyl; or 13 $SO_3M$;

$R_{14}$, $R_{15}$ and $R_{16}$ are each independently of one another $C_1$–$C_5$alkyl; or, if $n_1=0$, then $R_{15}$ and $R_{16}$, together with the linking nitrogen atom, are a heteroaromatic six-membered radical;

M is hydrogen; sodium; or potassium;

hal is a halogen atom;

$m_1$ is 1 to 5; and $n_1$ is 0 or 1.

The $C_1$–$C_{12}$alkyl radicals may be the groups methyl, ethyl, propyl, isopropyl, butyl, isobutyl, sec-butyl, tert-butyl, pentyl, hexyl, octyl, decyl or dodecyl.

$C_1$–$C_{18}$Alkoxy is straight-chain or branched radicals, such as methoxy, ethoxy, propoxy, butoxy, pentyloxy, hexyloxy, heptyloxy, octyloxy, isooctyloxy, nonyloxy, undecyloxy, dodecyloxy, tetradecyloxy or pentadecyloxy, hexadecyloxy, heptadecyloxy or octadecyloxy.

The phenyl-$C_1$–$C_3$alkyl radical is typically the benzyl, phenethyl or 2,2-dimethylbenzyl radical.

Halogen is fluoro, bromo or, preferably, chloro.

Suitable benzotriazole derivatives are preferably compounds of formula (1), wherein R is hydrogen, and $R_1$ is $C_1$–$C_{12}$alkyl.

Particularly preferred benzotriazoles are those of formula

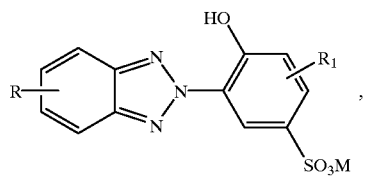
(3)

wherein

R, $R_1$ and M have the meanings stated above.

Very particularly preferred compounds are those of formula

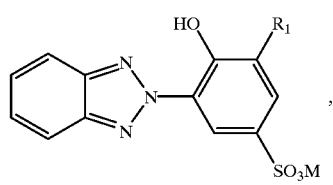
(4)

wherein $R_1$ is $C_1$–$C_{12}$alkyl; and

M is hydrogen; sodium; or potassium.

If $R_5$, $R_6$ or $R_7$ is a radical of formula (2e), then this radical preferably corresponds to formula

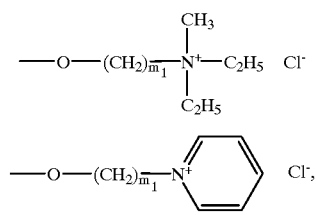

wherein $m_1$ is as defined above.

Preferred hydroxyphenyl-s-triazines conform to formula

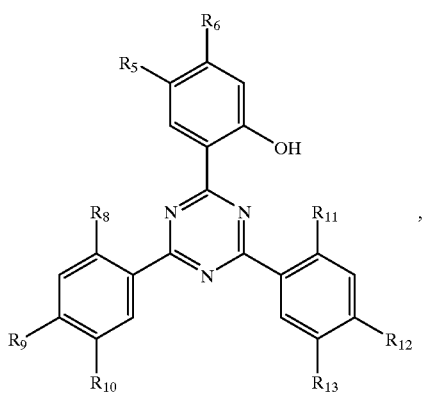
(5)

wherein $R_5$ is hydrogen; or $SO_3M$;

$R_6$ is hydrogen; hydroxy; $C_1$–$C_5$alkoxy; or a radical of formula (2e);

$R_8$, $R_9$, $R_{11}$ and $R_{12}$ are each independently of one another hydrogen or hydroxy; and $R_{10}$ and $R_{13}$ are each independently of the other hydrogen; or sulfo.

Particularly interesting compounds are those of formula (2), which contain at least one sulfo group or a radical of formula (2e).

Very particularly interesting compounds are hydroxyphenyl-s-triazines of formula (5), wherein $R_5$, $R_8$, $R_9$, $R_{10}$, $R_{11}$, $R_{12}$ and $R_{13}$ are hydrogen; and $R_6$ is a radical of formula (2e).

Likewise preferred are triazine compounds of formula (5), wherein $R_5$ is hydrogen; or $SO_3M$;

$R_6$ is hydroxy or $C_1$–$C_5$alkoxy;

$R_8$, $R_9$, $R_{11}$ and $R_{12}$ are hydroxy;

$R_{10}$ and $R_{13}SO_3M$; and

M is hydrogen; sodium; or potassium.

The following compounds are illustrative of the triazine derivatives which may be used according to this invention:

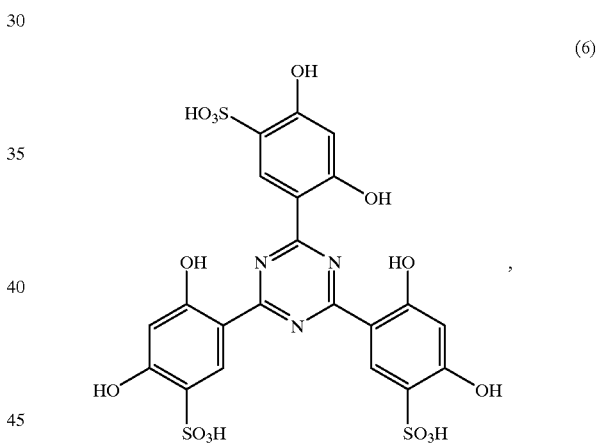
(6)

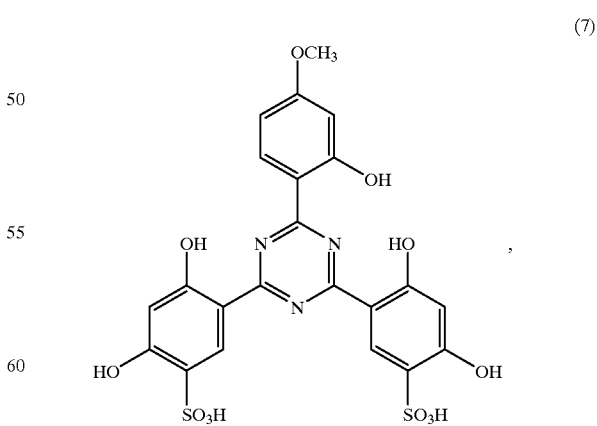
(7)

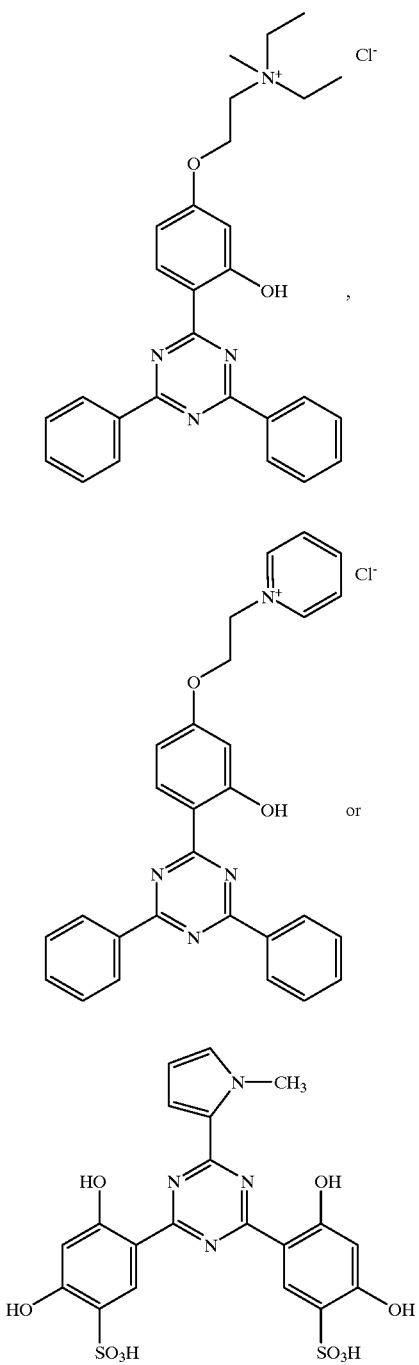

According to this invention it is also possible to use mixtures of UV absorbers of formulae (1) and (2) and also (3).

The benzotriazole derivatives of formulae (1), (3) and (4) are known compounds. Sodium salts of 3-[2'H-benzotriazol-(2')-yl]-4-hydroxybenzenesulfonic acids are known, inter alia, from EP-A-0 112 120. They are prepared by sulfonating the corresponding 2-[2'H-benzotriazol-(2')-yl]phenols with chlorosulfonic acid, these starting materials being prepared in accordance with the process of J. Rosevear and J. F. K: Wilshire, Aust. J. Chem. 1985, 38, 1163–1176.

The triazine derivatives of formulae (2) and (5) to (9) are also known from the literature and can be prepared in a manner known per se, e.g. by heating an amidine and an o-hydroxybenzenecarboxylate, preferably at about molar amounts in the ratio of 2:1, in boiling organic solvents [cf. U.S. Pat. No. 3,896,125 and Helv.Chim. Acta 55 (1972), 1566–1595].

The 3-[2'H-benzotriazol-(2)-yl]-4-hydroxybezenesulfonic acids of formulae (1), (3) and (4) and the 2-(2'-hydroxyphenyl)-s-triazines of formulae (2) and (5), which are used according to this invention, are known as UV absorbers for technical applications, e.g. for plastic materials, paints systems and films, natural or synthetic resins, waxy materials, rubber or also as light stabilisers in cosmetic formulations for the skin.

The benzotriazole and triazine derivatives used according to this invention are distinguished by having a high substantivity for human hair and guaranteeing high UV protection for hair.

Another object of this invention is the provision of a cosmetic formulation for hair, which comprises at least 0.25 to 5% by weight, based on the total weight of the composition, of a UV absorber of formula (1) and/or (2) and at least one auxiliary compatible with skin and hair.

The cosmetic formulation for hair can be prepared by physical mixing of the UV absorber or UV absorbers with the auxiliary or auxiliaries by customary methods, e.g. by simply stirring the individual components together.

Unless they are soluble in water, the novel UV absorbers used for cosmetic applications for hair usually have an average particle size in the range from 0.02 to 2, preferably from 0.05 to 1.5 and, very particularly preferably, from 0.1 to 1.0 $\mu$. The insoluble novel UV absorbers can be reduced to the desired particle size by customary methods, such as grinding in a nozzle mill, ball mill, vibratory mill or hammer mill. Grinding is preferably carried out in the presence of 0.1 to 30% by weight, more preferably of 0.5 to 15% by weight, based on the UV absorber, of a grinding auxiliary, such as an alkylated vinyl pyrrolidone polymer, a vinyl pyrrolidone/vinyl acetate copolymer, an acyl glutamate or, preferably, a phospholipid.

To prepare the novel cosmetic formulations for hair it is possible to use any conventionally usable emulsifier, typically one or several ethoxylated esters of natural derivatives, such as polyethoxylated ester of hydrogenated castor oil; or a silicone oil emulsifier, such as silicone polyol; a free or ethoxylated fatty acid soap; an ethoxylated fatty alcohol; a free or ethoxylated sorbitan ester; an ethoxylated fatty acid; or an ethoxylated glyceride.

In this case, the cosmetic formulation for hair may be used in the form of a shampoo, lotion, gel, or of an emulsion for rinsing, before or after shampooing, before or after dyeing or removing dye, before or after a perming or straightening process, in the form of a lotion, foam or gel for setting or treating hair, in the form of a lotion or a gel for brushing or waving hair, in the form of a hair lacquer, in the form of a composition for perming or straightening hair, for dyeing or removing dye.

It is possible to use, for example, the following cosmetic formulations for hair:

a₁) spontaneously emulsifying stock formulations, consisting of the UV absorber, PEG-6 $C_{10}$oxoalcohol and sorbitan esquioleate, which is charged with water and any quaternary ammonium compound, such as 4% minkamidopropyldimethyl-2-hydroxyethyl ammonium chloride or Quaternium 80;

a₂) spontaneously emulsifying stock formulation, consisting of the UV absorber, tributyl citrate and PEG-20 sorbitan monooleate, which is charged with water and any quaternary ammonium compound, such as 4% minkamidopropyldimethyl-2-hydroxyethyl ammonium chloride or Quaternium 80;

b) quat-doped solutions of the UV absorber in butyl triglycol and tributyl citrate;

c) dispersions of micronised UV absorbers obtained by known methods (precipitation from solutions or mixtures of solutions, grinding), having an average diameter of 0.05–1.0 μm in APG (e.g. Plantaren), and a quat (e.g. minkamidopropyldimethyl-2-hydroxyethyl ammonium chloride) in an aqueous formulation;

d) mixtures or solutions of the UV absorber with n-alkylpyrrolidone.

It is preferred to use cosmetic formulations for hair comprising, as UV absorber, a benzotriazole compound of formula (1), triethylene glycol butyl ether and tributyl citrate.

Of these formulations, those are very particularly preferred wherein the UV absorber is a benzotriazole compound of formula (4).

These last-mentioned formulations preferably comprise 25 to 50 parts of the benzotriazole compound of formula (1), preferably of formula (4), 40 to 80 parts of triethylene glycol butyl ether, and 0.5 to 5 parts of tributyl citrate.

In addition to the novel UV absorbers, the cosmetic formulation for hair can also contain one or more than one further UV protective of the following substance classes:

1. p-aminobenzoic acid derivatives, typically 2-ethylhexyl-4-dimethylaminobenzoate;
2. salicylic acid derivatives, typically 2-ethylhexyl salicylate;
3. benzophenone derivatives, typically 2-hydroxy-4-methoxybenzophenone and its 5-sulfonic acid derivative;
4. dibenzoylmethane derivatives, typically 1-(4-tert-butylphenyl)-3-(4-methoxyphenyl)propane-1,3-dione;
5. diphenylacrylates, typically 2-ethylhexyl-2-cyano-3,3-diphenylacrylate and 3-(benzofuranyl)-2-cyanoacrylate;
6. 3-imidazol-4-yl-acrylic acid and 3-imidazol-4-yl-acrylate;
7. benzofuran derivatives, preferably 2-(p-aminophenyl) benzofuran derivatives, disclosed in EP-A-582 189, U.S. Pat. No. 5,338,539, U.S. Pat. No. 5,518,713 and EP-A-613 893;
8. polymeric UV absorbers, such as the benzylidenemalonate derivatives described, inter alia, in EPA-709 080;
9. cinnamic acid derivatives, typically the 2-ethylhexyl-4-methoxycinnamate or isoamylate or cinnamic acid derivatives disclosed, inter alia, in U.S. Pat. No. 5,601,811 and WO 97/00851;
10. camphor derivatives, typically 3-(4'-methyl) benzylidenebornan-2-one, 3-benzylidenebornan-2-one, N-[2(and 4)-2-oxyborn-3-ylidenemethyl)benzyl] acrylamide polymer, 3-(4'trimethylammonium) benzylidenebornan-2-one methylsulfate, 3,3'-(1,4-phenylenedimethine)-bis(7,7-dimethyl-2-oxobicyclo-[2.2.1]heptane-1-methanesulfonic acid) and the salts thereof, 3-(4'-sulfo)benzylidenebornan-2-one and the salts thereof;
11. trianilino-s-triazine derivatives, typically 2,4,6-trianiline-(p-carbo-2'-ethyl-1'-oxi)-1,3,5-triazines as well as the UV absorbers disclosed in U.S. Pat. No. 5,332,568, EP-A-517 104, EP-A-507 691, WO 93/17002 and EP-A-570 838;
12. 2-hydroxyphenylbenzotriazole derivatives;
13. 2-phenylbenzimidazole-5-sulfonic acids and the salts thereof;
14. menthyl-o-aminobenzoate,
15. $TiO_2$ (coated differently), ZnO and mica.

The UV absorbers described in "Sunscreens", Eds. N. J. Lowe, N. A. Shaath, Marcel Dekker, Inc., New York and Basel, or in Cosmetics & Toiletries (107), 50ff (1992), can also be used as additional UV protectives in the inventive formulations for hair.

The cosmetic formulations for hair can also be used together with known antioxidants, such as vitamin E, carotinoids or HALS compounds.

The novel compositions can also comprise other useful auxiliaries, typically surfactants, thickeners, polymers, preservatives, fragrances, foam stabilisers, electrolytes, organic solvents, oils, waxes, degreasants, dyes and/or pigments, which serve to provide the cosmetic composition for hair with the same shade as that of the hair to be treated, as well as other auxiliaries conventionally used in hair cosmetics.

This invention also relates to a method of treating human hair to protect it from the harmful effects of UV radiation. This method comprises treating hair with a shampoo, lotion or gel, or with an emulsion for rinsing, before or after shampooing, before or after dyeing or removing dye, before or after a perming or straightening process; with a lotion, foam or gel for setting; with a lotion, foam or gel for brushing or waving; with a hair lacquer; with a composition for perming or straightening hair, for dyeing or removing dye, which shampoo, lotion, gel, emulsion, foam, hair lacquer or composition for perming, straightening, dyeing or removing dye comprises at least one UV absorber of formula (1) or (2).

The following non-limitative Examples illustrate the invention in more detail.

EXAMPLE 1

Determining the Affinity of UV Absorbers on Hair by Determining the Degree of Exhaustion from Formulations or Solutions 10 ml of a 10 mmolar UV absorber solution and 1 g of a lock of hair are defined in a glass vessel and shaken in reproducible manner. The decrease in UV absorber concentration in the test formulation or test solution is determined after 30 and 60 minutes using a spectrophotometer (see Table 1). The degree of exhaustion determined in this manner is a measure of the substantivity of the UV absorber or of the formulation in which it is present.

TABLE 1

Determination of the degree of exhaustion

| UV absorber used | degree of exhaustion [%] | |
| --- | --- | --- |
| | after 30 minutes | after 60 minutes |
| (101) [structure: 4-methoxy-2-hydroxyphenyl diphenyl triazine] | 27.0 | 39.0 |
| (102) [structure: benzotriazole with hydroxy, sec-butyl, and SO₃Na substituents] | 15.0 | 19.0 |
| (103) [structure: tris(dihydroxysulfophenyl)triazine] | 55.0 | 61.0 |
| (104) [structure: methoxy-hydroxyphenyl bis(dihydroxysulfophenyl) triazine] | 27.0 | 27.0 |

TABLE 1-continued

Determination of the degree of exhaustion

| UV absorber used | degree of exhaustion [%] | |
|---|---|---|
| | after 30 minutes | after 60 minutes |
| (105) | 25.0 | 25.0 |
| (106) | 21.0 | 24.0 |

EXAMPLE 2
Preparation of a Hair Rinse

| Composition | [g] |
|---|---|
| UV absorber of formula (102) | 1 |
| mixture of cetylstearyl alcohol and the polyadduct of 1 mol of cetylstearyl alcohol and 33 mol of ethlene oxide | 2 |
| monoethanol amide | 0.5 |
| xanthan gum | 0.8 |
| water | 95.7 |

The individual components are mixed, charged with preservatives and perfume oil and then adjusted to pH 6.5 with dilute HCl.

This gives a ready-to-use hair rinse which provides good and long-lasting UV protection for human hair.

What is claimed is:

1. A method of protecting human hair from the harmful effects of UV radiation by treating the hair with a cosmetic formulation comprising a protective amount of a benzotriazole of the formula

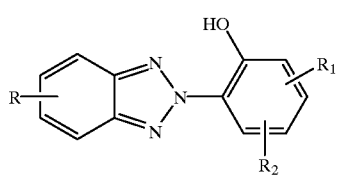

(1)

wherein

R is hydrogen or chloro, $R_1$ is $C_1$–$C_{12}$alkyl or phenyl-$C_1$–$C_3$alkyl, $R_2$ is $C_1$– to $C_4$alkyl or $SO_3M$, and M is hydrogen, sodium, or potassium.

2. A method according to claim 1, wherein in the compounds of formula (1)

R is hydrogen; and $R_1$ is $C_1$–$C_{12}$alkyl.

3. A method according to claim 1, wherein the compounds conform to formula

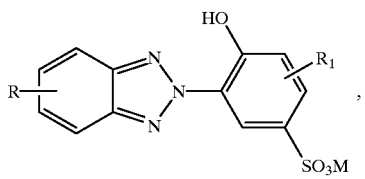

(3)

wherein

R, $R_1$ and M have the meaning claimed in claim 1.

4. A method according to claim 1, which comprises using compounds of formula

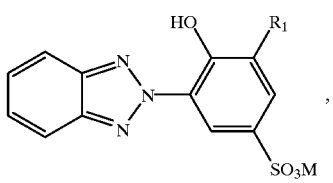

(4)

wherein $R_1$ is $C_1$–$C_{12}$alkyl; and

M is hydrogen; sodium; or potassium.

5. A cosmetic formulation which protects hair from the harmful effects of UV radiation, comprising 0.25 to 5% by weight, based on the total weight of the composition, of a UV absorber of the formula

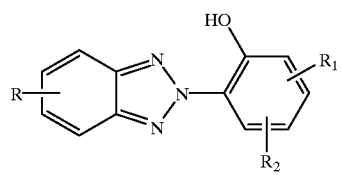

(1)

wherein $R_1$ is $C_1$–$C_{12}$alkyl or phenyl-$C_1$–$C_3$alkyl, $R_2$ is $C_1$– to $C_4$alkyl, or $SO_3M$, and M is hydrogen, sodium, or potassium, and at least one auxiliary compatible with skin and hair.

6. A formulation according to claim 5, wherein the UV absorber is a benzotriazole compound of formula (1), triethylene glycol butyl ether and tributyl citrate.

7. A formulation according to claim 6, wherein the UV absorber is a benzotriazole compound of formula (4).

8. A formulation according to claim 6, which comprises 25 to 50 parts of the benzotriazole compound of formula (1), 40 to 80 parts of triethylene glycol butyl ether, and 0.5 to 5 parts of tributyl citrate.

9. A formulation according to 5, which comprises as additional UV protectives p-aminobenzoic acid derivatives, salicylic acid derivatives, benzophenone derivatives, dibenzoylmethane derivatives, diphenylacrylates, benzofuran derivatives; cinnamic acid derivatives, camphor derivatives, trianilino-s-triazine derivatives, 2-hydroxyphenylbenzotriazole derivatives, 2-phenylbenzimidazole-5-sulfonic acids and the salts thereof, menthyl-o-aminobenzoate, $TiO_2$ (coated differently), ZnO and mica.

10. A formulation according claim 5, which additionally comprises antioxidants.

11. A method of treating natural or dyed human hair for protecting it from the harmful effects of UV radiation, which comprises treating hair with a shampoo, lotion or gel, or with an emulsion for rinsing, before or after shampooing, before or after dyeing or removing dye, before or after a perming or straightening process, with a lotion, foam or gel for setting, with a lotion, foam or gel for brushing or waving, with a hair lacquer, with a composition for perming or straightening hair, for dyeing or removing dye, which shampoo, lotion, gel, emulsion, foam, hair lacquer or composition for perming, straightening, dyeing or removing dye comprises at least one UV absorber of formula (1) as defined in claim 1.

* * * * *